(12) United States Patent
Ponsi (10) Patent No.: US 7,867,190 B2
(45) Date of Patent: Jan. 11, 2011

(54) COVERED SUCTION DEVICE

(75) Inventor: Lawrence G. Ponsi, Wheeling, IL (US)

(73) Assignee: Sage Products, Inc., Cary, IL (US)

( * ) Notice: Subject to any disclaimer, the term of this patent is extended or adjusted under 35 U.S.C. 154(b) by 0 days.

(21) Appl. No.: 11/766,556

(22) Filed: Jun. 21, 2007

(65) Prior Publication Data

US 2008/0319378 A1    Dec. 25, 2008

(51) Int. Cl.
   *A61M 1/00*   (2006.01)
   *A61M 5/32*   (2006.01)
(52) U.S. Cl. .......................................... 604/35; 604/192
(58) Field of Classification Search ................... 604/35, 604/162, 163, 165.04, 192
   See application file for complete search history.

(56) References Cited

U.S. PATENT DOCUMENTS 5,149,326 A * 9/1992 Woodgrift et al. ........... 604/163
6,500,142 B1 * 12/2002 Harreld et al. ................ 604/35
7,235,071 B2 * 6/2007 Gonnering .................... 606/41
2005/0234298 A1 * 10/2005 Kucklick et al. ............ 600/156

* cited by examiner

*Primary Examiner*—Kevin C Sirmons
*Assistant Examiner*—Bradley J Osinski
(74) *Attorney, Agent, or Firm*—Barnes & Thornburg LLP (57) ABSTRACT

A suction device which can protected before and after use. The suction device includes an elongated suction tube having a suction tip at one end. A retractable, protective sheath is connected to the tube and extends over the exposed length of the suction tube. A tip protector extends from the free end of the sheath, and includes an interference structure in the form of a plurality of spaced ribs protruding inwardly to engage and grip the suction tip. A hollow sheath housing is secured to the free end and a sheath inserter is secured to the suction tube proximate the connection end, with the sheath housing and the sheath inserter being shaped to insert the retractable sheath in the hollow sheath housing when the sheath is in a retracted position. The tip protector and the sheath housing can be portions of a unitary structure.

21 Claims, 7 Drawing Sheets

COVERED SUCTION DEVICE

BACKGROUND OF THE INVENTION

This invention relates to suction devices for medical purposes, and in particular to a covered suction device with a retractable, protective sheath with a tip protector secured to the sheath. A housing for the sheath, when retracted, is also provided.

Suction devices, for aspirating fluids from the body, are well known. Such suction devices typically include an elongated suction tube which is connectable at one end to a source of suction. The other end includes a tip having one or more holes leading to the suction tube to aid in aspiration as the suction device is being used.

The problem with prior suction devices is contamination. Suction devices are typically used over a period of time, and once first used, the device is contaminated. If the device is not protected in some manner, once it has been used, if it is laid aside for later use, it can further become contaminated by ambient contaminants, and transfer those contaminants to the patient the next time that it is used. Conversely, once it has been used on a sick patient, whatever ailment that is suffered by the patient can be passed from the suction device to whatever surface upon which it might be laid between uses, leading to contamination transferred from the patient to others. It is therefore important that the suction device be protected in some manner, both to protect the patient as well as others.

In the past, protection has been by means of providing a sterile surface upon which the suction device can be placed between uses. While that generally is satisfactory for largely eliminating passage of any contaminants from the patient, with the suction device being open to the ambient surroundings between uses, it still is subject to contamination by the surroundings, with that contamination then being passed back to the patient the next time that the suction device is used. Furthermore, once the device is contaminated by whatever means, returning it to a sterile surface contaminates the surface, and conversely, once the surface is contaminated, that can also be passed to a sterile device.

In U.S. Pat. No. 6,500,142, the disclosure of which is incorporated herein by reference, and which is assigned to the assignee of the present application, a covered suction device is provided which is a substantial improvement over those of the prior art. The present invention improves upon that of the '142 Patent, providing a simpler means to protect the suction tip and better means of accommodating the retracted sheath.

SUMMARY OF THE INVENTION

The invention is directed to a suction device comprising an elongated suction tube having opposite ends. A retractable sheath surrounds at least a portion of the suction tube, with the sheath having one end secured to the suction tube proximate a connection end of the suction tube, and the sheath having an opposite free end. A suction tip is provided at one end of the suction tube opposite the connection end, and in one form of the invention, a tip protector extends from the free end with the tip protector including a hollow tip housing and an interference structure shaped to engage and grip the suction tip.

In the preferred form of the invention, the interference structure comprises a plurality of spaced ribs protruding inwardly in the tip housing. Preferably, four of the ribs are spaced circumferentially and equally in the tip housing with opposite ribs having a gap therebetween no greater than the diameter dimension of the suction tip. In accordance with the preferred form of the invention, the ribs may be deformable to appropriately grip the suction tip.

In another form of the invention, as in the first form of the invention the suction device includes an elongated suction tube having opposite ends, a retractable sheath surrounding the suction tube, and a suction tip on the suction tube. In this form of the invention, a hollow sheath housing is secured to the free end and a sheath inserter is secured to the suction tube proximate the connection end, with the sheath housing and the sheath inserter being shaped to cooperate to insert the retractable sheath in the hollow sheath housing when the sheath is in a retracted position.

In this form of the invention, the hollow sheath housing comprises a cylinder extending around the suction tube and the inserter is shaped to fit within the cylinder. Preferably the inserter is cylindrical, having an outer wall spaced from the cylinder when the inserter is inserted within the cylinder.

Another form of the invention includes both the tip protector and the hollow sheath housing. In this form of the invention, the tip protector and the sheath housing are preferably portions of a unitary structure, although they can be separate elements, as well.

BRIEF DESCRIPTION OF THE DRAWINGS

The invention is described in greater detail in the following description of examples embodying the best mode of the invention, taken in conjunction with the drawing figures, in which.

DESCRIPTION OF EXAMPLES EMBODYING THE BEST MODE OF THE INVENTION

A suction device according to the invention is shown generally at 10 in the drawing figures. The suction device 10 is composed of an elongated suction tube 12 terminated by a connector 14 at one end and a suction tip at the other end. The connector 14 can be connected directly to the suction tube 12, or, as illustrated, the connector 14 can form part of a hollow grip 18 which is appropriately connected to the suction tube 12. That connection can be a permanent connection formed between the suction tube 12 and the grip 18, or can be a mechanical connection, such a force fit or a snap fit. The manner of connection of the tube 12 to the grip 18 forms no part of the invention, but if there is a mechanical connection, an appropriate connecting device, such as a latch 20, can be employed for connecting the hollow grip 18 to the suction tube 12 in a conventional fashion, which is not illustrated.

Figure 7:
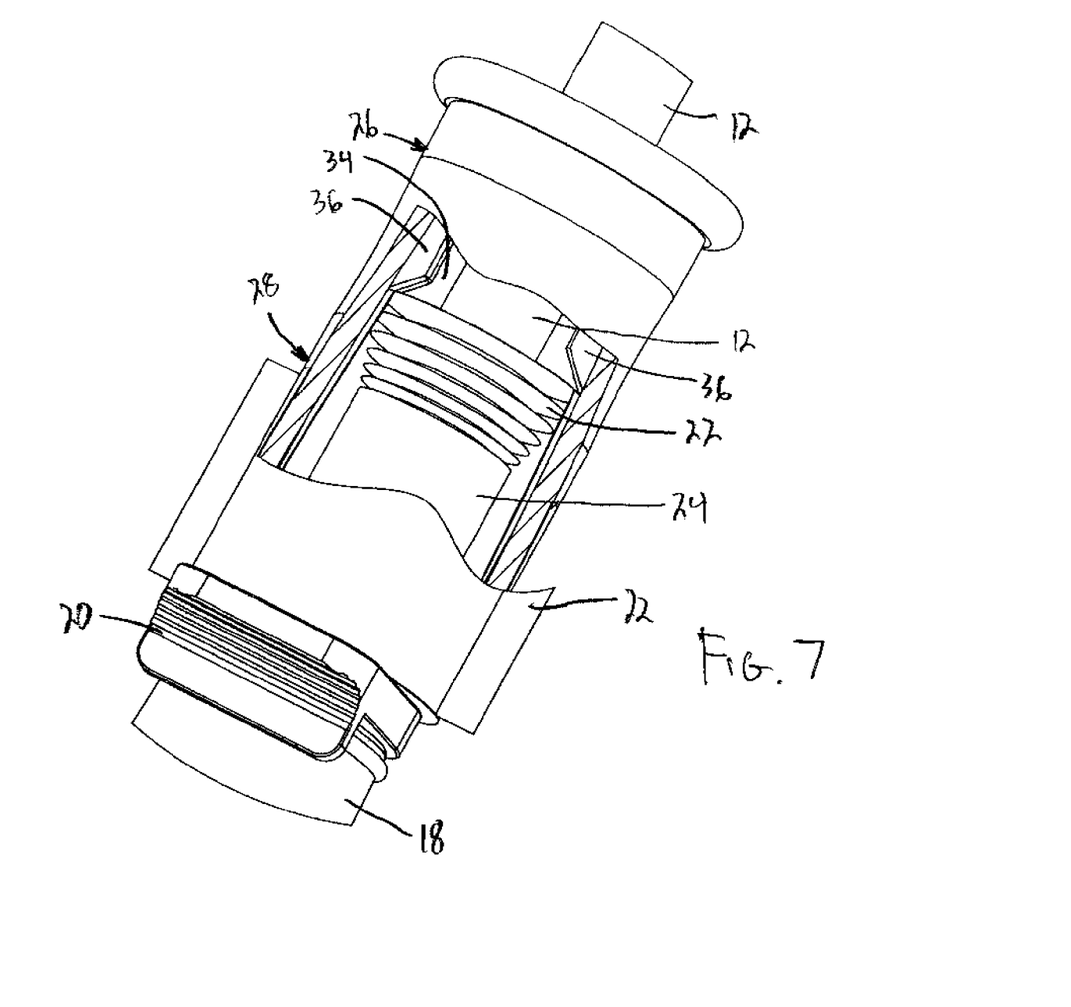
FIG. 7 is an enlarged, partial elevational view of the suction device illustrated in the FIG. 2, showing only the portion with the protective sheath retracted and being cut away to illustrate detail.

A retractable, protective sheath 22 surrounds at least a portion of the suction tube 12. The sheath 22 is attached as one end to a sheath inserter 24, whose purpose is described below, and which is secured at one end of the suction tube 12, as shown in FIG. 7. The opposite end of the sheath 22 is secured to a unitary structure comprising a tip protector 26 and a sheath housing 28, both of which are also described in further detail below. The sheath 22 is shown attached to the exterior of the sheath housing 28, and may be secured to the sheath housing 28 in any conventional manner so as to form a permanent connection.

As shown in the drawing figures, the suction tip 16 is an enlargement at one end of the suction tube 12. The suction tip 16 can be formed of a soft plastic material to cushion the tip when used, and is provided with an end aperture 30 and one or more radial apertures 32. Primary suction is through the end aperture 30, but if that aperture becomes clogged, suction can be through the radial apertures 32. Also, the radial apertures relieve suction if the end aperture is inadvertently pushed against tissue, which effectively seals the end aperture 30.

The tip protector 26 comprises a hollow tip housing 34 having a plurality of spaced ribs 36 which protrude inwardly in the tip housing 34. The ribs 36 form an interference structure to engage and grip the suction tip 16. While any number of ribs 36 can be employed as appropriate, it is preferred that there be four of the ribs 36 which are spaced circumferentially and equally in the tip housing 34, with ribs 36 opposing each other having a gap there inbetween which is no greater than the diameter of the suction tip 16 captured between the ribs 36. While the ribs 36 are preferably substantially rigid extensions of the material of the tip housing 36, similar to the formation of the suction tip 16, the ribs 36 can also deformable. Formation of the ribs 36 and the tip 16 is such that when the tip 16 is engaged by the ribs 36, the tip protector 26 is held in place by the ribs 36 on the tip 16 until the tip protector 26 is physically displaced. Other forms of an interference structure to engage and grip the suction tip 16 can be used, as well.

The sheath housing 28 is cylindrical and is considerably larger in diameter than the suction tube 12, extending around the suction tube 12 as shown. The sheath inserter 24 is shaped to fit within the cylindrical sheath housing, as best shown in FIG. 7, in order to facilitate gathering of the sheath 22 within the sheath housing 28, as described below in further detail.

It is preferred that the tip protector 26 and the sheath housing 28 be portions of a unitary structure, and are preferably formed of plastic, although any other appropriate material could be used, as well. If the tip protector 26 and the sheath housing 28 are separate structures, they are appropriately affixed to one another, such as by gluing, welding, or appropriate other connection.

Figure 2:
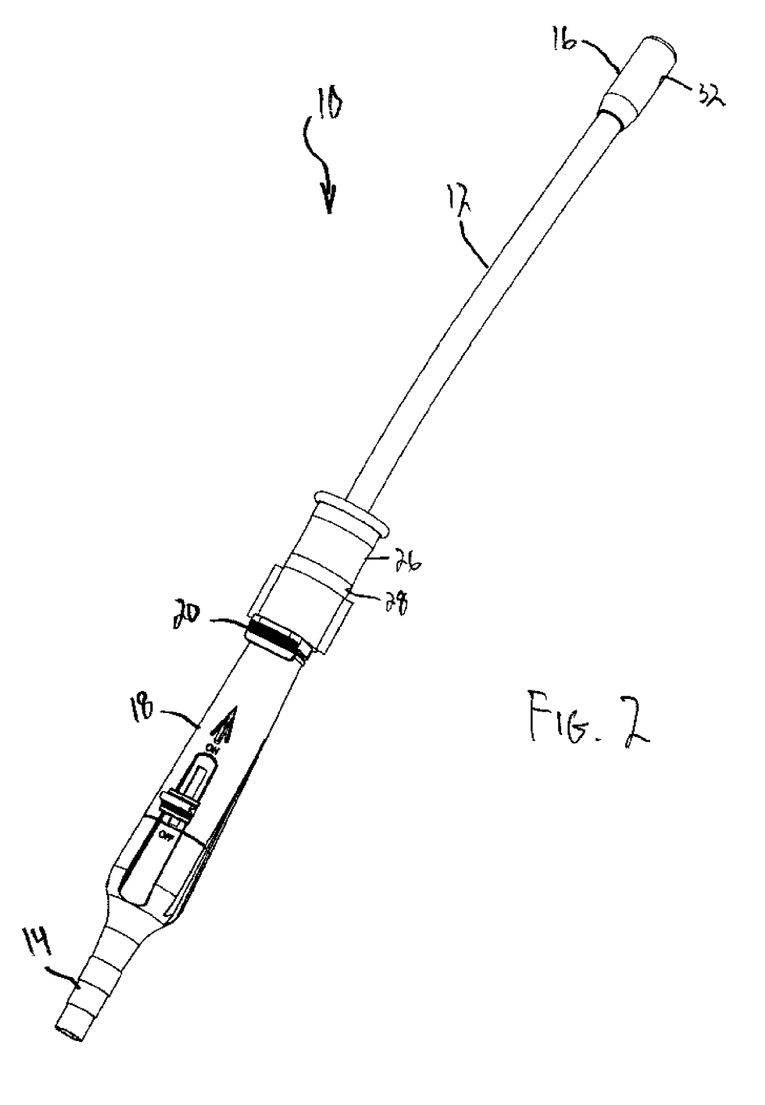
FIG. 2 is an elevational illustration similar to that of FIG. 1, but with the protective sheath retracted.
Figure 3:
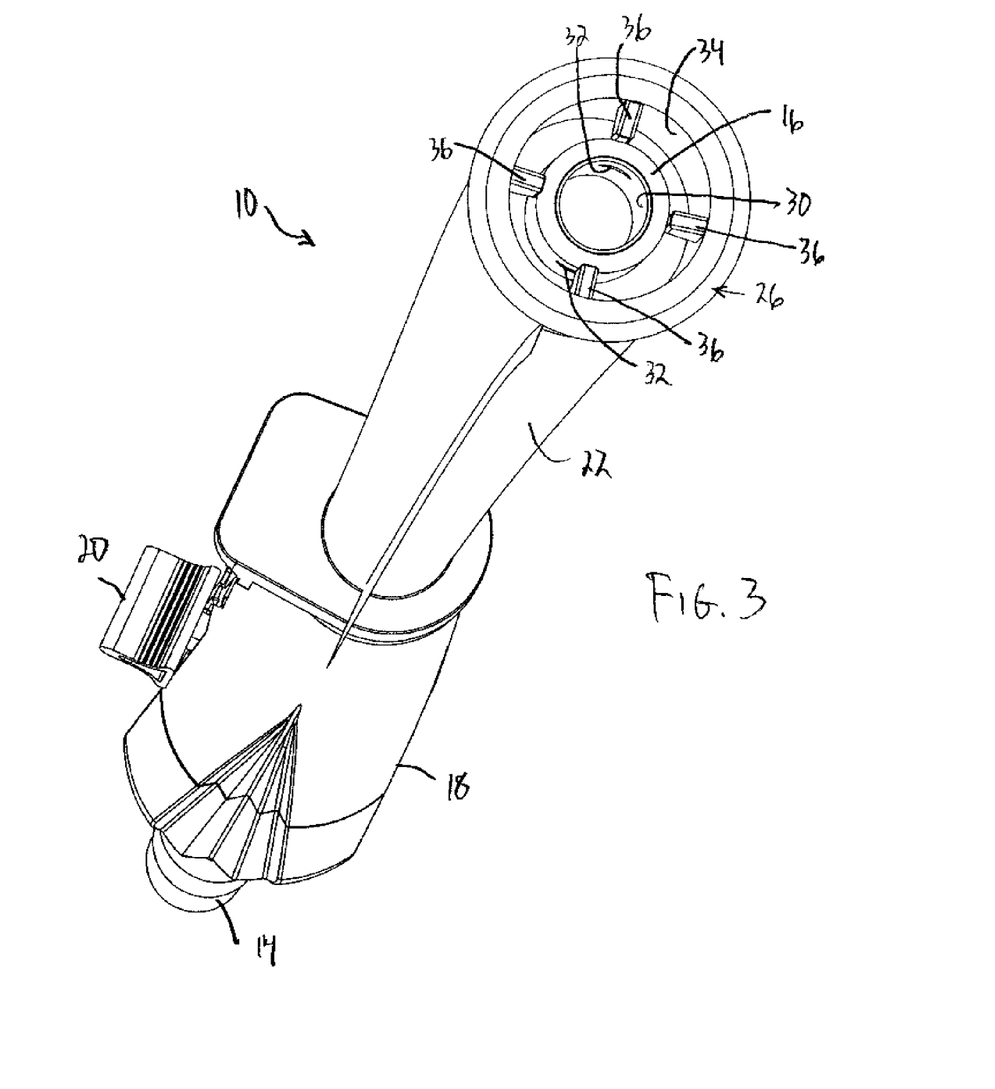
FIG. 3 is an enlarged perspective view of the suction device according to the invention with the protective sheath being deployed and being viewed toward the suction tip.
Figure 4:
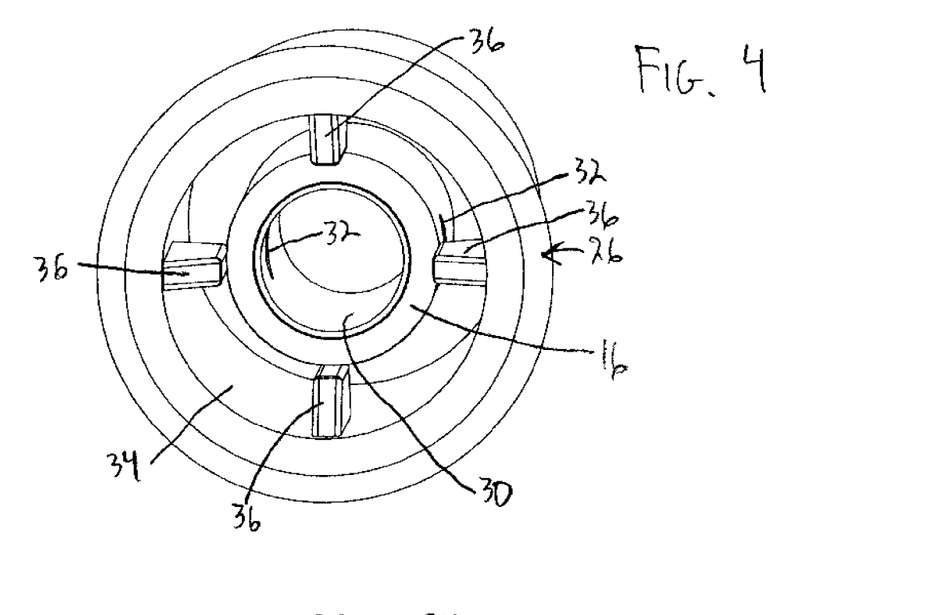
FIG. 4 is a further enlarged view of the suction tip, similar to FIG. 3 but from a different perspective, and having upstream portions of the suction device beneath the tip removed for clarity.
Figure 5:
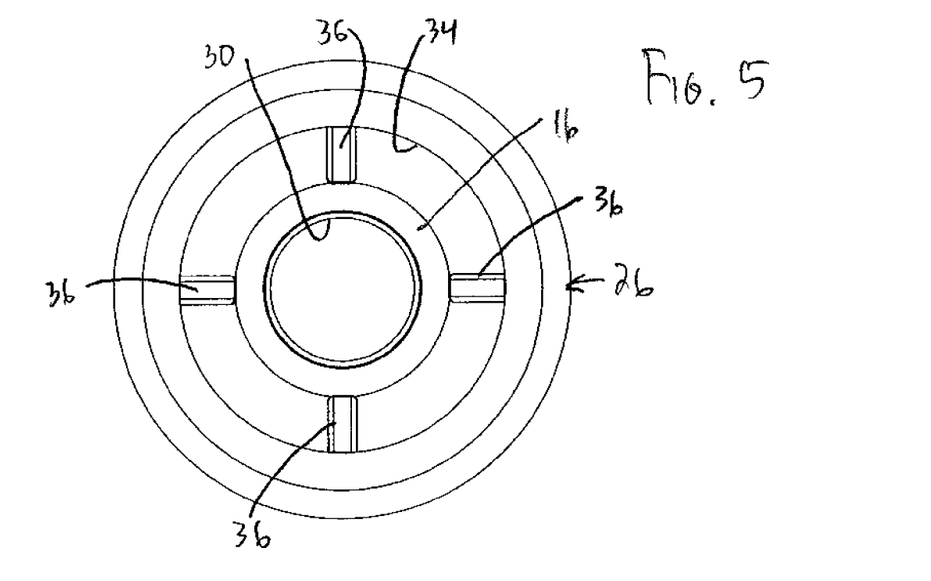
FIG. 5 is a view similar to FIG. 4, but in an elevational view looking directly at the suction tip.
Figure 6:
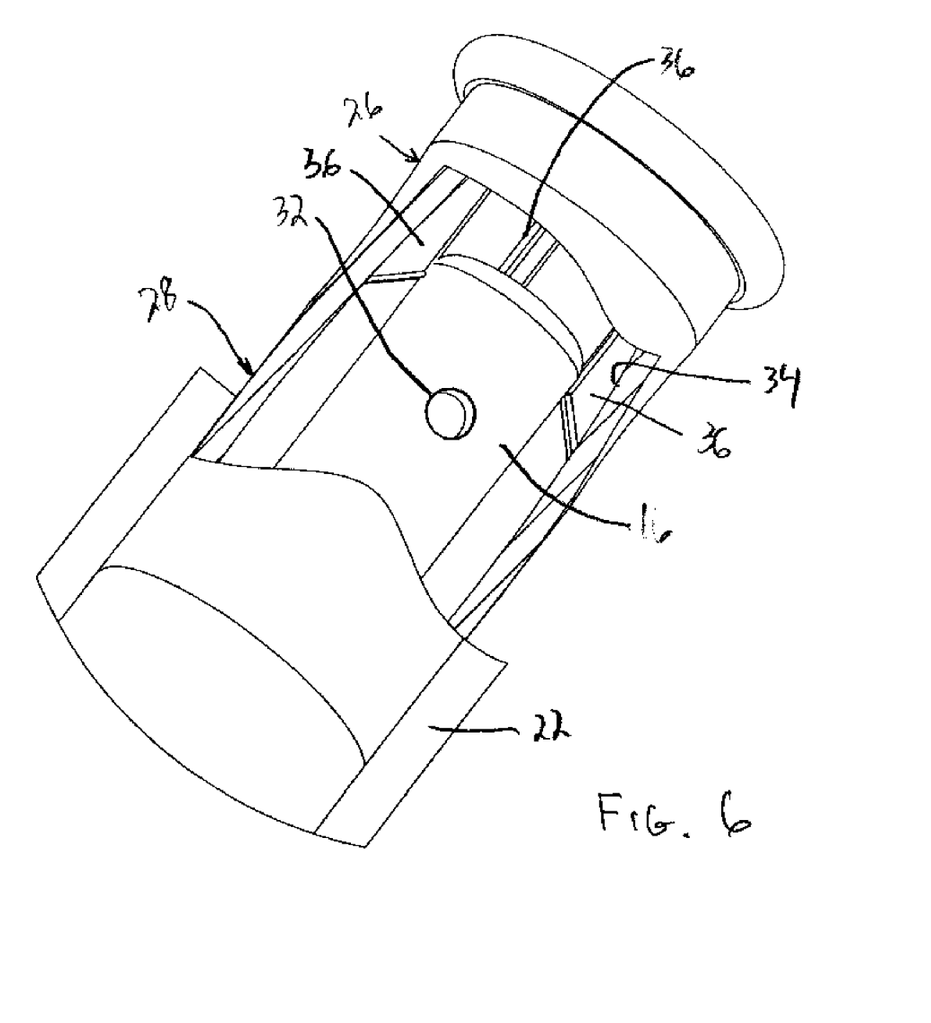
FIG. 6 is a partial perspective view of the tip portion of the suction device according to the invention with the protective sheath deployed as illustrated in FIG. 1, with portions beneath the tip being removed for purposes of clarity and with portions being cut away to illustrate detail.
Figure 8:
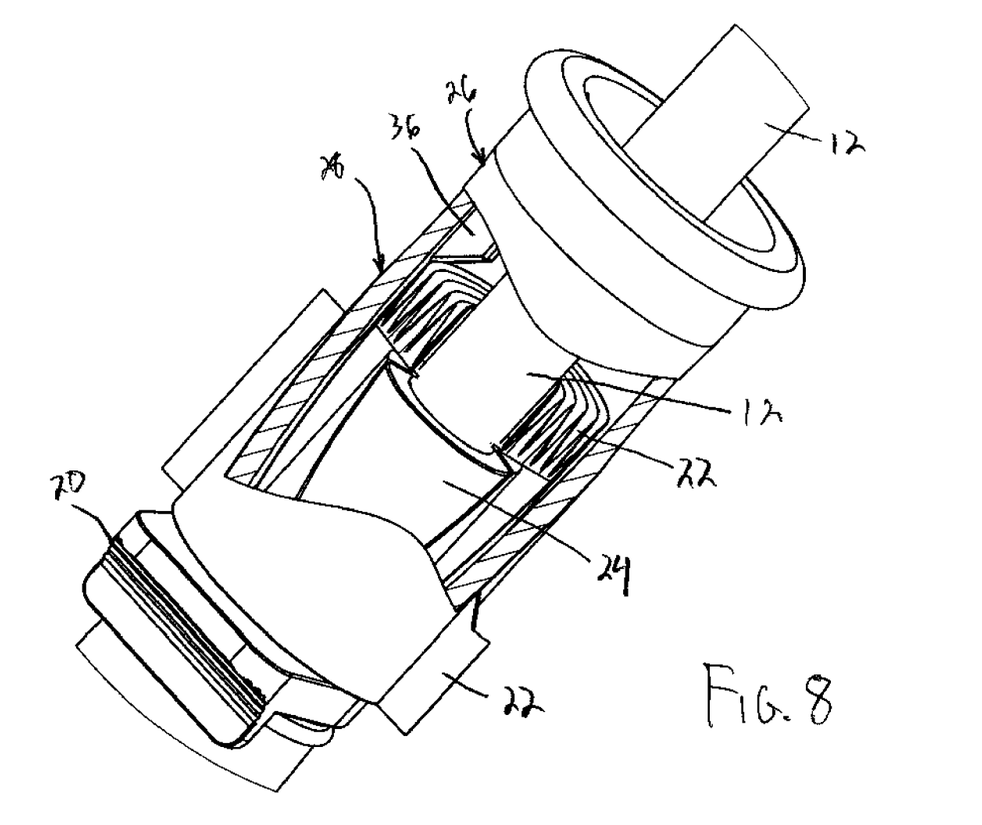
FIG. 8 is a perspective view of the portion shown in FIG. 7, and showing collapsing of the retractable sheath in a different orientation.

The sheath housing 28 is where the sheath 22 is gathered when the tip protector 26/sheath housing 28 is withdrawn along the suction tube 12 to the position shown in FIGS. 2, 7 and 8. As best illustrated in FIGS. 7 and 8, the sheath 22 is gathered in an accordion fashion in the sheath housing 28, and interference between the bulk of the gathered sheath 22 and the sheath housing 28 retains the tip protector 26/sheath housing 28 in the retracted position illustrated when withdrawn. As also illustrated, the sheath inserter 24 is smaller in diameter than the internal dimension of the sheath housing 28.

The sheath inserter 24 is cylindrical in shape with its outer wall having a smaller diameter than the inner diameter of the sheath housing 28 such that the outer wall of the sheath inserter 24 is spaced from the inner wall of the sheath housing 28 when the inserter 24 is in the housing 28. The sheath 22 is preferably formed of a thin, plastic material in the nature of a film which can be readily gathered as the tip protector 26/sheath housing 28 is retracted from the suction tip 16. Thus, as illustrated in FIGS. 7 and 8, when the tip protector 26/sheath housing 28 is fully retracted, the sheath 22 is appropriately gathered in the sheath housing 28. This protects the sheath 22 from an inadvertent tear, as well as keeping it out of the way when the suction device 10 is used.

Figure 1:
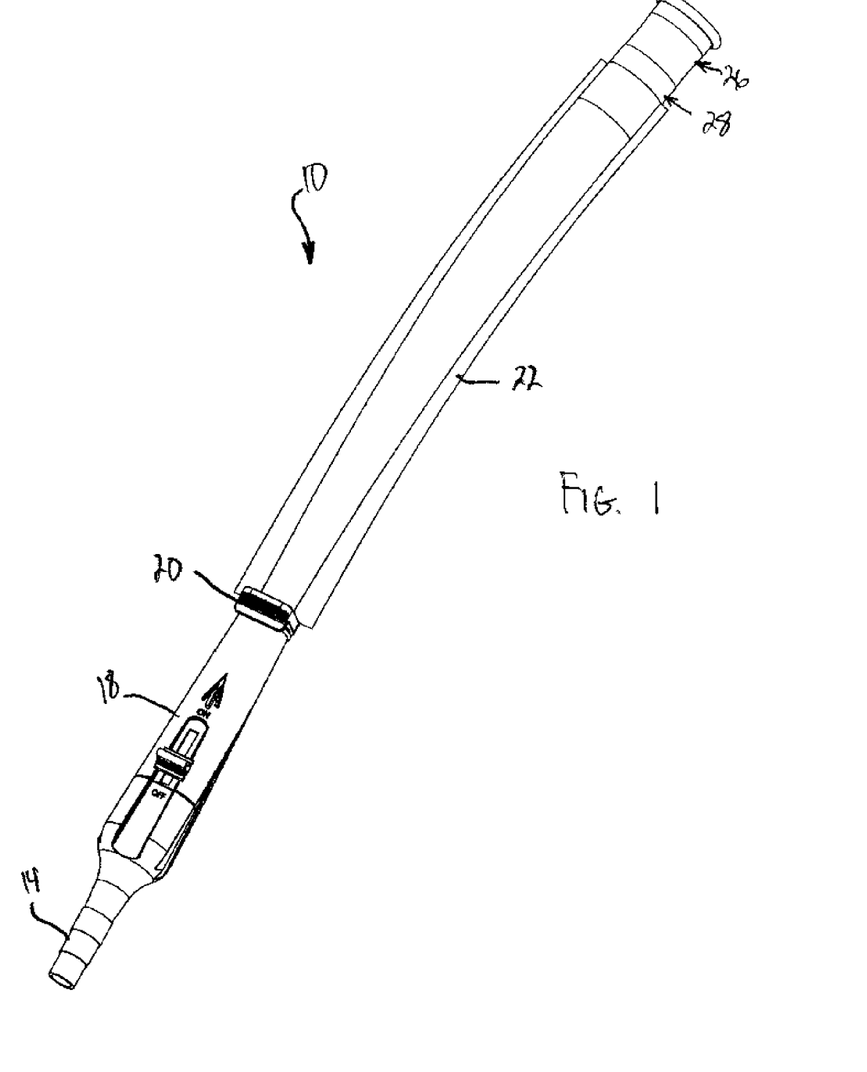
FIG. 1 is an elevational illustration of a suction tube according to the invention, with the protective sheath being deployed.

In use, the suction device 10 is normally provided as illustrated in FIG. 1, with the protective sheath 22 fully deployed with the tip protector 26 engaged on the suction 16. The connector 14 is then connected to an appropriate source of suction (not illustrated).

When the suction device 10 is to be used to aspirate fluids, the user simply grips the tip protector 26/sheath housing 28 and slides it down the suction tube 12 to the fully retracted position shown in FIGS. 2, 7 and 8. The sheath 22 is gathered within the sheath housing 28 in this orientation, and the gathered sheath 22, in the housing 28, holds the tip protector 26/sheath housing 28 in the retracted position. The suction device 10 can then be used. After use, the tip protector 26/sheath housing 28 is simply returned along the suction tube 12 to the suction tip 16, where the suction tip 16 is gripped by the ribs 36, retaining the tip protector 26 and sheath housing 28 in place. In this manner, the suction device 10 can be used and reused, protecting the tube 12 and the tip 16 from either passing contamination to the ambient surroundings, or being contaminated by those surroundings. The suction device 10 thus provides an effective means of avoiding contamination during its use. Normally, after use, the suction device 10 is then discarded.

As illustrated in FIGS. 7 and 8, when the sheath 22 is gathered within the sheath housing 28, the sheath 22 is collapsed and two collapsed orientations are shown in FIGS. 7 and 8. Since the sheath 22 is a pliable film, its gathering may be more haphazard than shown in FIGS. 7 and 8, but in any event, the sheath 22 is gathered in the sheath housing when in the retracted position.

Various changes can be made to the invention without departing from the spirit thereof or scope of the following claims.

What is claimed is:

1. A suction device comprising,
   a. an elongated suction tube having opposite ends, said suction tube having a first diameter,
   b. a retractable sheath surrounding at least a portion of said suction tube, said sheath having one end secured to said suction tube proximate a connection end of said suction tube, and said sheath having an opposite free end,
   c. a suction tip at an end of said suction tube opposite said connection end, said suction tip having a second diameter greater than said first diameter, and
   d. a tip protector extending from said free end, said tip protector including a hollow tip housing and an interference structure longitudinally engaging said suction tip on opposite sides and shaped to engage and grip said suction tip to retain said tip protector on said suction tip, said interference structure comprising at least three ribs protruding inwardly in said tip housing and having a gap no greater than said second diameter but greater than said first diameter.

2. The suction device according to claim 1, including four of said ribs spaced circumferentially and equally in said tip housing with opposite ribs having a gap therebetween no greater than a diameter dimension of said suction tip.

3. The suction device according to claim 1, in which at least one of said rib and said suction tip is deformable.

4. A suction device comprising
   a. an elongated suction tube having opposite ends,
   b. a retractable sheath surrounding at least a portion of said suction tube, said sheath having one end secured about said suction tube proximate a connection end of said suction tube, and said sheath having an opposite free end,
   c. a suction tip at an end of said suction tube opposite said connection end, and
   d. a hollow sheath housing secured to said free end and a sheath inserter secured to said suction tube proximate said connection end, said sheath inserter being spaced from and inserted within said sheath housing when said sheath is in a retracted position, said sheath inserter being generally cylindrical and larger in diameter than said suction tube, and said sheath housing and said sheath inserter being shaped to cooperate to locate said retractable sheath in said hollow sheath housing when said sheath is in a retracted position, with said sheath being gathered at friction between gathered pleats of the gathered sheath and the sheath housing retains the sheath housing in the retracted position.

5. The suction device according to claim 4, in which said hollow sheath housing comprises a cylinder extending around said suction tube and said inserter is shaped to at least partially fit within said cylinder.

6. The suction device according to claim 5, in which said inserter is cylindrical, having an outer wall spaced from said cylinder when inserted therewithin.

7. A suction device comprising
   a. an elongated suction tube having opposite ends, said suction tube having a first diameter,
   b. a retractable sheath surrounding at least a portion of said suction tube, said sheath having one end secured about said suction tube proximate a connection end of said suction tube, and said sheath having an opposite free end,
   c. a suction tip at an end of said suction tube opposite said connection end, said suction tip having a second diameter greater than said first diameter,
   d. a tip protector extending from said free end, said tip protector including a hollow tip housing and an interference structure longitudinally engaging said suction tip on opposite sides and shaped to engage and grip said suction tip, said interference structure comprising at least three ribs protruding inwardly in said tip housing and having a gap no greater than said second diameter but greater than said first diameter, and
   e. a hollow sheath housing secured to said free end and a sheath inserter secured to said suction tube proximate said connection end, said sheath housing and said sheath inserter being shaped to cooperate to insert said retractable sheath in said hollow sheath housing when said sheath is in a retracted position.

8. The suction device according to claim 7, in which said tip protector and said sheath housing are portions of a unitary structure.

9. The suction device according to claim 7, including four of said ribs spaced circumferentially and equally in said tip housing with opposite ribs having a gap therebetween no greater than a diameter dimension of said suction tip.

10. The suction device according to claim 9, in which at least one of said ribs and said suction tip is deformable.

11. The suction device according to claim 7, in which said hollow sheath housing comprises a cylinder extending around said suction tube and said inserter is shaped to fit within said cylinder.

12. The suction device according to claim 11, in which said inserter is cylindrical, having an outer wall spaced from said cylinder when inserted therewithin.

13. A suction device comprising
   a. an elongated suction tube having opposite ends, said suction tube having a first diameter,
   b. a retractable sheath surrounding at least a portion of said suction tube, said sheath having one end secured to said suction tube proximate a connection end of said suction tube, and said sheath having an opposite free end,
   c. a suction tip at an end of said suction tube opposite said connection end, said suction tip having a second diameter greater than said first diameter, and
   d. a tip protector extending from said free end, said tip protector including an always open hollow tip housing and an interference structure shaped to longitudinally engage a portion of the suction device at least on opposite sides to retain said tip protector in an extended position with said tip housing encompassing at least a part of said suction tip, said interference structure comprising at least three ribs protruding inwardly in said tip housing and having a gap no greater than said second diameter but greater than said first diameter.

14. The suction device according to claim 13, including four of said ribs spaced circumferentially and equally in said tip housing with opposite ribs having a gap therebetween no greater than a diameter dimension of said suction tip.

15. The suction device according to claim 13, in which at least one of said rib and said suction tip is deformable.

16. A suction device comprising
   a. an elongated suction tube having opposite ends, said suction tube having a first diameter,
   b. a retractable sheath surrounding at least a portion of said suction tube, said sheath having one end secured about said suction tube proximate a connection end of said suction tube, and said sheath having an opposite free end,
   c. a suction tip at an end of said suction tube opposite said connection end, said suction tip having a second diameter greater than said first diameter,
   d. a tip protector extending from said free end, said tip protector including a hollow tip housing and an interference structure shaped to longitudinally engage a portion of the suction device at least on opposite sides to retain said tip protector in an extended position encompassing at least a portion of said suction tip, said interference structure comprising at least three ribs protruding inwardly in said tip housing and having a gap no greater than said second diameter but greater than said first diameter, and
   e. a hollow sheath housing secured to said free end and a sheath inserter secured to said suction tube proximate said connection end, said sheath housing and said sheath inserter being shaped to cooperate to locate said retractable sheath in said hollow sheath housing when said sheath is in a retracted position.

17. The suction device according to claim 16, in which said tip protector and said sheath housing are portions of a unitary structure.

18. The suction device according to claim 16, including four of said ribs spaced circumferentially and equally in said tip housing with opposite ribs having a gap therebetween no greater than a diameter dimension of said suction tip.

19. The suction device according to claim 18, in which at least one of said ribs and said suction tip is deformable.

20. The suction device according to claim 16, in which said hollow sheath housing comprises a cylinder extending around said suction tube and said inserter is shaped to fit within said cylinder.

21. The suction device according to claim 20, in which said inserter is cylindrical, having an outer wall spaced from said cylinder when inserted therewithin.

* * * * *

UNITED STATES PATENT AND TRADEMARK OFFICE
CERTIFICATE OF CORRECTION

| | | |
|---|---|---|
| PATENT NO. | : 7,867,190 B2 | Page 1 of 1 |
| APPLICATION NO. | : 11/766556 | |
| DATED | : January 11, 2011 | |
| INVENTOR(S) | : Lawrence G. Ponsi | |

It is certified that error appears in the above-identified patent and that said Letters Patent is hereby corrected as shown below:

Claim 4, at column 5, lines 25-28 should read as follows: --with said sheath being gathered at one end of said sheath inserter such that friction between gathered pleats of the gathered sheath and the sheath housing retains the sheath housing in the retracted position--

Signed and Sealed this
Twenty-first Day of June, 2011

David J. Kappos
*Director of the United States Patent and Trademark Office*